(12) United States Patent
Kumar et al.

(10) Patent No.: US 8,068,650 B2
(45) Date of Patent: Nov. 29, 2011

(54) LESION QUANTIFICATION AND TRACKING USING MULTIPLE MODALITIES

(75) Inventors: Shashi Kumar, Bangalore (IN); Xiang Zhou, Exton, PA (US); Karthikeyan Kaliyamoorthi, Karnataka (IN); Venkat Raghavan Ramamurthy, Yardley, PA (US); Arun Krishnan, Exton, PA (US)

(73) Assignees: Siemens Information Systems, Ltd., Bangalore (IN); Siemens Medical Solutions USA, Inc., Malvern, PA (US)

( * ) Notice: Subject to any disclaimer, the term of this patent is extended or adjusted under 35 U.S.C. 154(b) by 825 days.

(21) Appl. No.: 12/056,575

(22) Filed: Mar. 27, 2008

(65) Prior Publication Data

US 2008/0260222 A1      Oct. 23, 2008

Related U.S. Application Data

(60) Provisional application No. 60/909,005, filed on Mar. 30, 2007.

(51) Int. Cl.
*G06K 9/00* (2006.01)
*A61B 5/05* (2006.01)

(52) U.S. Cl. .................. 382/128; 600/407; 600/425

(58) Field of Classification Search .............. 382/128, 382/129, 130, 131, 132, 133, 134, 103; 600/407, 600/410, 425, 427, 436, 509, 529; 250/363.04; 378/4, 21–27, 901; 128/916, 920, 22
See application file for complete search history.

(56) References Cited

U.S. PATENT DOCUMENTS 5,787,886 A * 8/1998 Kelly et al. ............... 600/407
5,871,013 A * 2/1999 Wainer et al. ............. 600/407
6,983,034 B2 * 1/2006 Wang et al. ................. 378/4
7,760,941 B2 * 7/2010 Bornemann et al. ...... 382/173
2006/0025669 A1 * 2/2006 Ramamurthy et al. ... 600/407

OTHER PUBLICATIONS

Grosu et al., "Validation of a Method for Automatic Image Fusion (BrainLAB System) of CT Data and 11C-Methionine-PET Data for Stereotactic Radiotherapy Using a LINAC: First Clinical Experience", Int. J. Radiation Biol. Phys., vol. 56, No. 5, 2003, pp. 1450-1463.

Sibomana et al., "Head and Neck Multimodality Volumes Visualization Methods", 2002 IEEE Nuclear Science Symposium Conference Record, Norfolk, VA, Nov. 10-16, 2002, New York, NY, IEEE, US, vol. 2, Nov. 10, 2002, pp. 1282-1286.

Huber et al., "Dual-Modality PET/Ultrasound Imaging of the Prostate", Nuclear Science Symposium Conference Record, 2005 IEEE Wyndham El Conquistador Resort, Puerto Rico, Oct. 23-29, 2005, Piscataway, NJ, USA, IEEE, vol. 4, Oct. 23, 2005, pp. 2187-2190.

Rizzo et al., "Multi-Modal Medical Image Integration to Optimize Radiotherapy Planning in Lung Cancer Treatment", Annals of Biomedical Engineering, vol. 32, No. 10, 2004, pp. 1399-1407.

Lancaster et al., "Automated Talairach Atlas for Functional Brain Mapping", Human Brain Mapping, Wiley-Liss, New York, NY, US, vol. 10, Jan. 1, 2000, pp. 120-131.

* cited by examiner

*Primary Examiner* — Abolfazl Tabatabai
(74) *Attorney, Agent, or Firm* — Peter Withstandley

(57) ABSTRACT

A method for lesion detection includes acquiring pre-therapy medical image data from a first modality. Post-therapy medical image data is acquired from a second modality. A transformation matrix for transforming from an image space of the first modality to an image space of the second modality is calculated. A volume of interest is defined from the medical image data of the first modality. The volume of interest includes one or more lesions. The volume of interest is automatically copied to the medical image data of the second modality using the calculated transformation matrix. Treatment is directed to the lesion using the medical image data of the second modality including the copied volume of interest data.

16 Claims, 4 Drawing Sheets

LESION QUANTIFICATION AND TRACKING USING MULTIPLE MODALITIES

CROSS-REFERENCE TO RELATED APPLICATION

The present application is based on provisional application Ser. No. 60/909,005, filed Mar. 30, 2007, the entire contents of which are herein incorporated by reference.

BACKGROUND OF THE INVENTION

1. Technical Field

The present disclosure relates to lesion tracking and, more specifically, to multi-modal lesion quantification and tracking.

2. Discussion of Related Art

Computer aided medical diagnosis is the process of using computer analysis of medical images to help a medical practitioner such as a radiologist diagnose and treat patients. Computer aided medial diagnosis may use medical images obtained from a number of imaging modalities. Common modalities include computer tomography (CT), positron emission tomography (PET), single photon emission computed tomography (SPECT), magnetic resonance (MR), and ultrasound. These various modalities may be used to image anatomical and functional aspects of the patient so that disease, injury and congenital disorder may be accurately diagnosed.

Computer aided medical diagnosis is particularly useful in the field of oncology. For example, medical practitioners may use computer aided medical diagnosis to help track the progression of one or more lesions. Moreover, the nature of the lesions may be automatically quantified to more accurately track the lesions.

Lesion quantification and tracking may prove useful for both following the natural progression of a lesion and to measure the effectiveness of treatment. For example, imaging studies may be performed both pre-therapy and post therapy, and lesions may be quantified and tracked at both of the two studies. By comparing the quantified values for the lesion in both studies, the effectiveness of the applied treatment may be gauged.

As discussed above, many modalities may be used to obtain medical images. Some modalities such as the CT are best suited for illustrating anatomical structure, while other modalities such as the PET are best suited for illustrating functional aspects. For example, image information obtained from a PET scan may be well suited to track the progress of a lesion while image information obtained from a CT scan may be well suited to provide the structural information necessary to accurately direct radiation therapy to the site of the lesion. Moreover, various other differences in obtaining and processing images from various modalities leads to acquired images that differ vastly in overall appearance and diagnostic value.

As the acquisition of certain imaging modalities such as CT scans may lead to exposure to ionizing radiation that may be harmful to the patient and may incur substantial expenses, it may be desirable to minimize the total number of imaging studies performed. Accordingly, benefit may be derived from approaches that can perform efficient lesion quantification and tracking using diverse modalities so that the number of imaging studies required may be minimized.

However, because the characteristics of images from various modalities differs so substantially, it may be difficult on one hand for medical practitioners to effectively compare data obtained from various modalities and it may be difficult on the other hand for medical practitioners to use the same modalities that are used for tracking and quantification for the accurate direction of therapy.

SUMMARY

A method for lesion detection includes acquiring medical image data from a first modality. Medical image data is acquired from a second modality. A transformation matrix for transforming from an image space of the first modality to an image space of the second modality is calculated. A volume of interest is defined from the medical image data of the first modality. The volume of interest includes one or more lesions. The volume of interest is automatically copied to the medical image data of the second modality using the calculated transformation matrix.

Treatment may be directed based on structural information provided by the medical image data of the second modality and the volume of interest copied thereto. The treatment may include radiotherapy. The first modality may be a functional modality and the second modality may be a structural modality. The first modality may be a PET or a SPECT and the second modality may be a CT or MR.

The volume of interest may be defined from manual segmentation performed on one or more image slices of the medical image of the first modality. The volume of interest may be defined from a placement of a predetermined shape within the medical image of the first modality.

The method may additionally include creating a radiotherapy object for directing radiotherapy by marking the volume of interest on the image data first modality, wherein the first modality is a PET.

A method for lesion tracking includes acquiring medical image data from a first modality at a first point in time. A volume of interest is defined from the medical image data of the first modality, wherein the volume of interest includes a lesion. One or more original quantified characteristics are calculated for the lesion based on the defined volume of interest. Medical image data is acquired from a second modality at a second point in time. The volume of interest is transformed to a second modality space and the transformed volume of interest is copied to the medical image data of the second modality. One or more updated quantified characteristics are calculated for the lesion for the copied volume of interest within the medical image data of the second modality. The one or more original quantified characteristics for the lesion are compared with the one or more updated quantified characteristics for the lesion to determine how the lesion has changed from the first point in time to the second point in time.

The first modality may be a functional modality and the second modality is a structural modality. The first modality may be a PET or a SPECT and the second modality may be a CT or MR. The first point in time may occur prior to performance of a treatment and the second point in time may occur after the performance of the treatment. The determination of how the lesion has changed from the first point in time to the second point in time may be a determination of how the lesion has responded to the performance of the treatment.

The volume of interest may be defined from manual segmentation performed on one or more image slices of the medical image of the first modality. The volume of interest may be defined from a placement of a predetermined shape within the medical image of the first modality. The one or more original quantified characteristics and the one or more updated quantified characteristics may include a minimum feature size, a maximum feature size, or an average feature size.

A computer system includes a processor and a program storage device readable by the computer system, embodying a program of instructions executable by the processor to perform method steps for lesion quantification and tracking. The method includes acquiring medical image data from a functional modality. A volume of interest is defined from the medical image data of the functional modality. One or more original quantified characteristics are calculated for the defined volume of interest. Medical image data is acquired from a structural modality. The volume of interest is transformed to a second modality space and the transformed volume of interest is copied to the medical image data of the structural modality. One or more updated quantified characteristics are calculated for the copied volume of interest within the medical image data of the structural modality.

The functional modality may be a PET or a SPECT and the structural modality is a CT or MR. The medical image data from the functional modality may be acquired prior to performing a course of treatment and the medical image data from the structural modality may be acquired after performing the course of treatment and the original quantified characteristics are compared to the updated quantified characteristics to determine a response to the course of treatment.

The volume of interest may be defined from a placement of a predetermined shape within the medical image of the first modality. The one or more original quantified characteristics and the one or more updated quantified characteristics may include a minimum feature size, a maximum feature size, or an average feature size.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
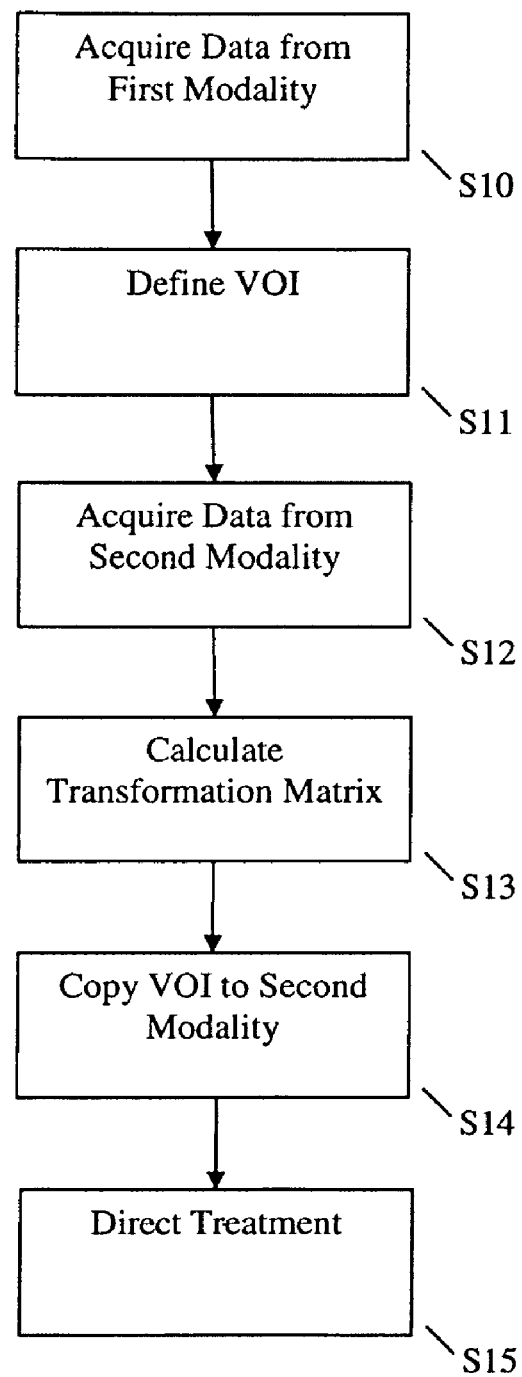
FIG. 1 is a flow chart illustrating a method for detecting lesions according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide methods and systems for computer aided medical diagnosis and treatment of lesions, including lesion quantification and tracking that are able to exploit image data from multiple imaging modalities.

As discussed above, medical images may be obtained from various modalities such as CT, PET, SPECT, MR and Ultrasound. Computerized reconstruction of the image data may produce three-dimensional volumes. These image volumes may then be used to analyze the health of the patient, for example, by performing lesion quantification and tracking.

While the image data produced from one modality may not be easily comparable to the image data produced from another modality, exemplary embodiments of the present invention seek to provide approaches for reconciling image data from diverse modalities. Reconciled image data may then be used to track the progression of a lesion over time even in cases where differing modalities are used at different times. This may include, for example, methods for quantifying lesions in a modality-independent manner so that quantitative lesion assessments generated from one modality may be meaningfully compared with quantitative lesion assessments generated from another modality.

When lesions are quantified and tracked in a modality-independent manner, the flexibility of the medical practitioner is substantially increased, patient exposure of ionizing radiation may be minimized, and unnecessary expenses related to additional imaging studies may be avoided.

Implementation of exemplary embodiments of the present invention may provide the ability to mark and/or segment lesions in multiple modalities simultaneously. When image data is obtained by more than one modality, the two image data sets may be co-registered such that when a lesion is marked and/or segmented within the first image data set, the mark and/or segmentation may be projected into the second image data set. For example, a medical practitioner may mark the presence of a lesion in a PET data set. Marking of a lesion may be performed more easily within a PET data set than in data sets of other modalities because of the functional data that is captured by the PET scan. The marking of the lesion may give rise to a volume of interest (VOI) within the PET data set. The marking may then be projected into a CT data set for the same patient. In so doing, the VOI may be created within the CT data set. Accordingly, the lesion identified from the PET image data set may be automatically marked within the CT image data set. Because the CT image data set may contain greater structural detail than the PET image data set, the marking of the lesion in the CT image data set may provide a suitable guide for directing treatment such as radiotherapy and surgery, directly to the site of the lesion.

Implementations of exemplary embodiments of the present invention may provide the ability to quantify and track an identified lesion over time using image scans obtained using diverse modalities during the course of therapy, for example, pre-therapy and post-therapy.

As discussed above, the co-registration of anatomical information from modalities such as CT and MR with the functional information from modalities such as PET and SPECT may be clinically useful. Co-registration may be performed to account for the differences in voxel dimensions between the relatively high-resolution CT and MR images as compared to the relatively low-resolution PET and SPECT images.

In co-registering the image data sets of the various modalities, common voxel dimensions may be defined. These common voxel dimensions may then be used by both anatomical and functional image data sets to provide a way to facilitate co-registration. The common voxel dimensions should be defined with sufficient resolution to ensure that the Nyquist criterion are satisfied and that there are enough samples of each voxel to avoid quantification errors.

VOIs constructed may then use the common voxel dimension so that the size of each VOI is the same in different modalities. A registration matrix may then be created to appropriately transform marked lesions from one modality space to another modality space. The registration matrix may be used to transform the coordinates of a VOI drawn within one image modality to another image modality. Replication of the VOI involves a copying of spatial information of the drawn VOI within the first image data set to the second image data set. The replication of the VOI between modalities may be further complicated by the prospect that the first image modality may have been acquired pre-therapy while the second image modality may have been acquired post-therapy. In such a case, the VOI drawn on the first image modality, pre-therapy is considered the master VOI. After the VOI has been copied to the second image modality, post therapy, the copied image is considered the slave VOI.

When VOIs are copied from pre-therapy to a post-therapy study a master is created in that study if the corresponding modality pair is available. For example, where CT and a PET scans have each been performed pre-therapy, and thereafter, only a PET scan is performed post-therapy, a VOI may be constructed on the pre-therapy PET. This VOI may thus be considered the master VOI in pre-therapy. When copied across time to the post-therapy dataset, the copied VOI from the pre-therapy PET to the post-therapy PET may be considered a post-therapy master. However, if only a CT scan is performed post-therapy, then the VOI that is transformed to the CT space is considered a slave VOI.

The VOI may be copied in this way either from an image of a first modality to an image of a second modality or from a pre-therapy image to a post-therapy image. When the VOI is copied from the first modality to the second modality, the VOI within the first modality is considered the master VOI while the VOI copied to the second modality is considered the slave VOI. Exemplary embodiments of the present invention may also involve copying of the VOI from a first modality pre-therapy to a second modality post-therapy.

The VOI may be defined as a polygon, for example, a sphere, free-drawn shape, ellipse, ellipsoid, etc. The VOI may contain a set of points in three-dimensions to be drawn over an image. Thus, the VOI may be represented as a binary volume, indicating that each voxel of the image is either included in the VOI or excluded from the VOI. The binary volume of the VOI may be super-sampled to have a resolution that is greater than the resolution of the image data the VOI is drawn on. Super-sampling may prevent pixilation when the VOI is displayed on low-resolution image data sets such as PET images. Additionally, super-sampling may provide for more accurate calculation of properties such as VOI volume and may also provide a common platform to create VOIs counterparts on other modalities. This also helps maintaining consistency between quantification values like volume across modalities that may differ in the sizes.

The VOI may be created, for example, by drawing a contour over a two-dimensional slice of the 3D image volume. The contour drawn over the two-dimensional slice may then be copied to each of the other slices of the image volume or separate contours may be drawn for each image slice. Alternatively, contours may be drawn for some image slices, for example, a first image slice and a last image slice, and the three-dimensional shape of the VOI may be automatically generated by interpolation and/or extrapolation.

The binary volume that represents the VOI may be expressed as a matrix of four vectors, namely: a row vector (Rv), column vector (Cv), normal vector (Nv), and position vector (Pv). In the matrix of vectors, the row vector may be represented along the y-axis, the column vector may be represented along the x-axis, and the normal vector may be represented along the z-axis. The position vector may be represented as a starting point pf the binary volume. After the binary structure is defined, voxel information for the VOI may be stored in the binary structure by storing the voxel state as either high or low.

Because the VOI is drawn on the 3D image volume, and the 3D image volume is made up of discrete image slices with interpolated planes there between, it is possible for the VOI to be drawn upon an interpolated plane. In such cases, the VOI may be modified to begin on a nearest actual image slice rather than an interpolated plane. Such treatment may further simplify the quantification of lesions.

However, where multiple data sets have been co-registered with a registration matrix, as described above, it is possible that an image volume will have been rotated, thereby complicating the finding of the nearest actual image slice. In such cases, the contour may be first converted to a plane parallel to the actual image slices (the reference volume plane) and then the VOI may be modified to begin on the nearest actual image slice.

There may be multiple approaches for defining VOIs according to exemplary embodiments of the present invention. For example, the VOI may be a contour-based VOI. In this case, the VOI may be created by stacking one or more 2D contours to form the 3D VOI. Each contour may be individually drawn or one or more contours may be automatically generated from contours that are individually drawn. Where n represents the number of contours, the VOI may be defined as the sum of the contours:

$$VOI = C1 + C2 + C3 + \ldots + Cn$$

VOIs may be defined by a 3D shape object, for example, an ellipsoid or a sphere. The dimensions of the shape object may be set so as to capture the physical structure of interest within the image volume, for example, including a lesion. The nature of the shape object used may be predetermined or may be selected, by the medical practitioner, from a set of shape objects according to which shape best fits the structure of interest.

VOIs may be defined as Normal VOIs, where the VOI is defined as a single region mask, for example, a bounding region mask (BRM). The region mask may be used for quantification of the VOI.

Iso VOIs or thresholded VOIs are those VOIs which allow the user to identify the VOI boundary. Iso VOIs and threshold VOIs may further allow the user to define the image voxels to be used in quantification by allowing a threshold to be set with the marked VOI.

In a thresholded or iso VOI, two region masks may be used to represent the VOI. For example, both the BRM and a threshold region mask (TRM) may be combined to define the VOI. Here, the TRM may be used for the quantification of the VOI while the BRM may be used to calculate the initial threshold values.

For contour based ISO VOIs the BRM may be constructed by combining the BRMs of the associated contours. TRMs may be created after the construction of BRM on a per VOI basis, where it is the TRM that is quantified.

Statistical values, for example, Min, Max, Average, Volume, Std Deviation etc. may be calculated for the constructed VOI. Quantification values may be computed for the entire VOI based on its constituent contours for each 2D slice of the 3D VOI. For ISO VOIs the quantification values may be computed based on the threshold regions. Quantification values themselves may be calculated using either a histogram or a hash-table, for example, as described below.

Along with the quantification values such as the statistical values listed above, certain other values like max-diameter, max-size and the determination of which slice the max-value occurs on may also be calculated and reported along with the VOI. The max-diameter value may be defined as the maximum size of the VOI in three dimensions. The max-size may be defined as the size of each VOI along the X, Y and Z axes in the orientation in which it was created. These values may be clinically useful as they may provide information that helps to determine the extent of the lesion.

The progress of lesions, for example, lesion growth or response to treatment, may be gauged by comparing VOIs drawn across studies conducted at various points in time. A percentage change in lesion size may be calculated between the VOIs drawn across studies and this figure, and other data derived from the VOIs may assist the medical practitioner in planning treatment.

A database or other storage implementation may be used to store created VOIs for later retrieval. VOIs may then be retrieved from the database for comparison purposes to track the lesion over time. Examples of suitable database systems include Digital Imaging and Communications in Medicine (DICOM) systems. According to an exemplary embodiment of the present invention, VOIs may be stored in a DICOM system as DICOM RT objects. Created VOIs stored as DICOM RT objects may then be loaded into therapy planning systems. VOI construction may be performed automatically from medical image data stored in the DICOM system for VOIs created on either anatomical (for example, CT) or functional (for example, PET) modalities.

When used in this manner, a medical practitioner such as a radiologist may identify a lesion on a PET dataset, perform appropriate thresholding, and make the thresholded region available on an anatomical counterpart such as a CT dataset. The threshold may then be saved as a RT object.

Volume data sets obtained from different medical modalities may contain multiple 2D slices. VOI creation, display and various other operations that may be performed on VOI must generally be performed in a relatively short time to satisfy the demands of the clinical environment. Various forms of optimization may be performed to achieve desired times. Examples of such optimization techniques are described below.

For example, VOIs may be generated in accordance with one or more threshold values that define what voxels are to be included in the VOI and what voxels are to be excluded. If not satisfied with the VOI as generated, a user may adjust the threshold values to create a more inclusive or less inclusive VOI. Recalculating of the VOI with respect to the revised threshold values should be performed in real time so that the user does not have to wait as the VOI is recalculated.

According to one technique for facilitating the generation of VOI in real time as thresholds are changed, a hash table may be used. The hash table may maintain a list of voxel coordinates and values in the volume that may be used to recalculate VOIs. Then, a thresholding operation range may be set by a user. The thresholding may be applied from the minimum to the maximum pixel value, by traversing the hash table for the same range and setting the corresponding voxels, the coordinates of which are present in the hash table. Accordingly, values such as min, max, volume, average of the VOI, may be quickly calculated. The existing hash table may be used to compute the threshold region masks for as long as the VOI remains unchanged. If the VOI is edited, the hash table may be updated. The use of the hash table may save the time spent in performing the threshold operation.

For any dataset or volume existing in a 3D space, the coordinates that are used to define the spatial information of the dataset/volume may be referred to as the world-space coordinate.

As discussed above, the binary volumes may be at a higher resolution than the source volumes. This may result in a single voxel being queried multiple times for a particular world-space coordinate. The adverse effects of the repeated queries may be mitigated by caching the voxel value for a particular coordinate. The cache may be then refreshed when the calculated coordinate value changes. The same procedure may be extended in 3D. Such a technique may be referred to as single-line caching.

The process of creating the hash table and histogram may be further optimized for speed by caching a local sub-volume of voxel values that contribute to the VOI. There may be multiple calls to a single voxel from more than one super-sampled voxel. An appropriate offsets may be added to the cache so that the correct voxel values may be quickly accessed. The time taken for creation of this cache itself may be minimized by applying the technique described above. Such a technique may be referred to as on-demand caching.

Super sampling of the VOI may involve the calculation of the voxel dimensions of the binary volume.

From a performance perspective, the calculated voxel dimension may be varied such that a high-resolution VOI is created for smaller VOIs, for example, when the diameter is less than 3 cm. A more coarse resolution may be used for bigger VOIs when the diameter is greater than 9 cm. Where multiples datasets are involved, the Vx, Vy and Vz dimensions may be calculated for the primary series of the first medical imaging study.

FIG. 1 is a flow chart illustrating a method for detecting lesions according to an exemplary embodiment of the present invention. First, the medical image may be acquired from a first modality (Step S10). The first modality may be a functional modality, for example, a PET or a SPECT. The medical image may either be directly acquired from the imaging device or it may be loaded from a medical image database. Next, a volume of interest (VOI) may be defined from within the medical image data of the first modality (Step S11). The VOI may encompass one or more lesions. The VOI may be defined from manual segmentation performed on one or more image slices of the medical image of the first modality, for example, as discussed in detail above. Additionally, or alternatively, the VOI may be defined by the placement of a predetermined shape within the medial image of the first modality, also as described in detail above.

A medical image may then be squired from a second modality (Step S12). The second modality may be a structural modality, for example, a CT or MR. The medical image may either be directly acquired from the imaging device or it may be loaded from the medical image database.

A transformation matrix may then be calculated for transforming between the first image space and the second image space (Step S13). Thus, the transformation matrix may be indicative of the spatial relationship between the first image space and the second image space. The transformation matrix may then be used to copy the VOI from the medical image of the first modality to the medical image of the second modality (Step S14).

Treatment may then be directed to a patient using the medical image data of the second modality which may display the internal structure of the patient (Step S15). The copy of the VOI copied to the image data of the second modality may direct the treating physician as to where to apply the treatment. Treatment may include radiotherapy and/or surgery.

Figure 2:
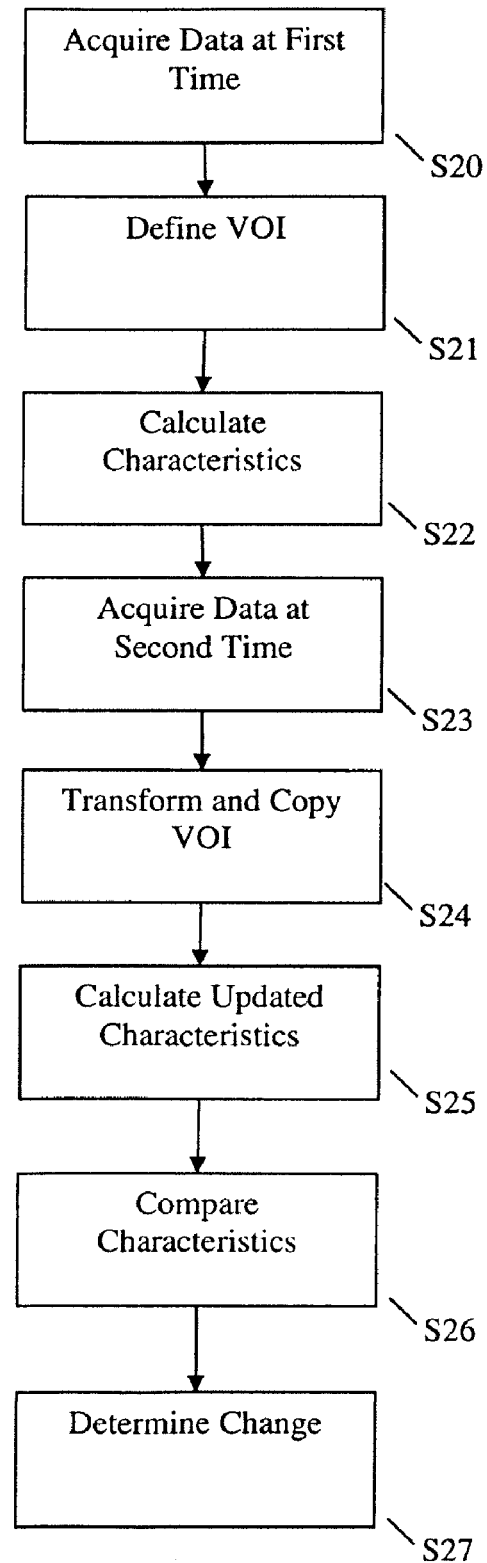
FIG. 2 is a flow chart illustrating a method for lesion tracking according to an exemplary embodiment of the present invention.

FIG. 2 is a flow chart illustrating a method for lesion tracking according to an exemplary embodiment of the present invention. First, medical image data may be acquired from a first modality at a first point in time (Step S20). As discussed above, the first modality may be a functional modality, for example, a PET or SPECT. The first point in time may be a point in time prior to the administration of treatment, for example, radiotherapy or chemotherapy. Then, a VOI may be defined from the medical image data of the first modality at the first point in time (Step S21). The VOI may include one or more lesions.

Next, one or more quantified characteristics of the image data of the first modality may be calculated, based on the position of the VOI (Step S22). These calculated characteristics may be original quantitative characteristics because they are derived from image data acquired prior to treatment. At a second point in time after treatment, medical image data from a second modality may be acquired (Step S23). The VOI may be transformed and copied to the medical image data of the second modality (Step 24). Transformation may be performed using a transformation matrix as discussed above.

One or more quantified characteristics of the image data of the second modality may be calculated, based on the position of the copied VOI (Step S22). The image data of the second modality may represent an image obtained at a second point in time, for example, after treatment. Quantitative characteristics may be calculated from the image data of the second modality (Step S25). This may be updated quantitative characteristics because it may represent how the lesion has changed over time. Accordingly, the characteristics at the site of the VOI may have changed from the first point in time to the second point in time. Where no therapy is administered, the passage of time may have been responsible for a change in the characteristics at the site of the VOI.

The quantitative characteristics from the image taken at the first point in time, for example, prior to treatment, may be compared with the quantitative characteristics from the image taken at the second point in time, for example, after treatment (Step S27). The comparison may provide insight into the progression or remission of the lesion, for example, as a result of the treatment and/or the passage of time.

Accordingly, by employing methods according to exemplary embodiments of the present invention, a medical practitioner may first choose to image a patient with a functional imaging device, for example a PET, as the functional imaging device may be most useful for rendering an effective diagnosis of the lesion. However, at a later point in time, the medical practitioner may wish to image the patient using a structural imaging device, for example, a CT. The structural imaging device may be most useful for guiding therapy to the site of the lesion, for example, the CT may provide information useful in directing radiotherapy or performing surgery. Exemplary embodiments of the present invention may provide a way of gauging the progression of the lesion from the first imaging to the second imaging using quantitative measures even when the two imaging studies were performed using diverse modalities that are difficult to compare.

Figure 3:
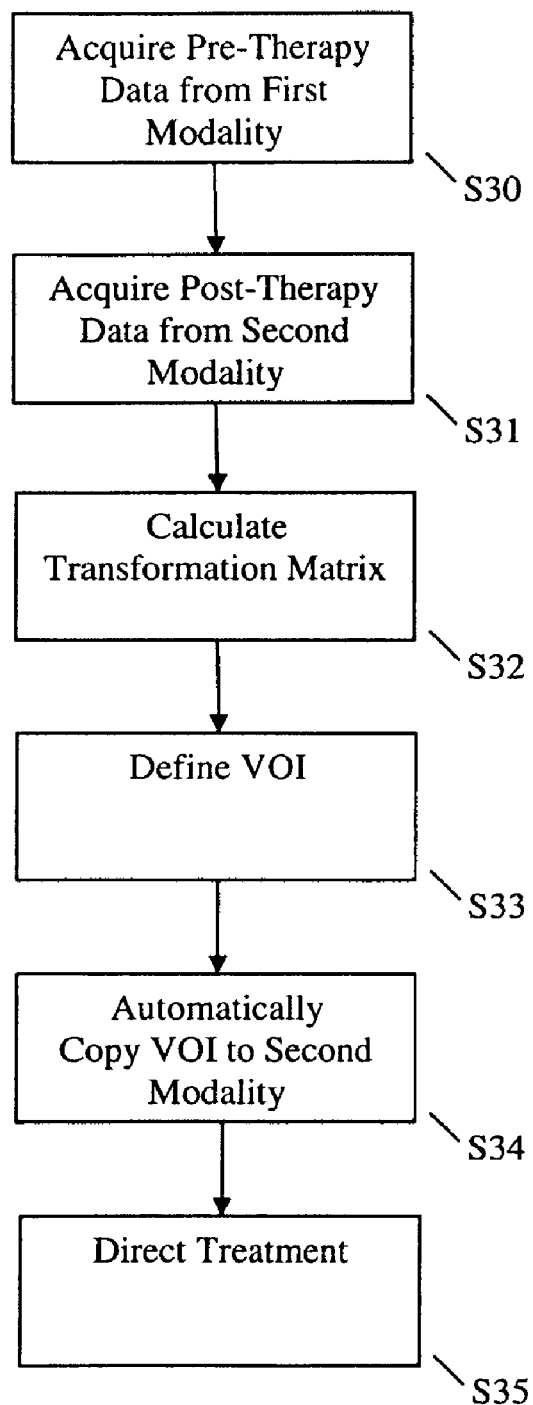
FIG. 3 is a is a flow chart illustrating a method for directing radiotherapy based on medical image data acquired from multiple modalities according to an exemplary embodiment of the present invention.

FIG. 3 is a flow chart illustrating a method for directing radiotherapy based on medical image data acquired from multiple modalities according to an exemplary embodiment of the present invention. First, medical image data may be acquired from the first modality (Step S30). Then, medical image data may be acquired from the second modality (Step S31). A transformation matrix for transforming a structure from the space of the medical image data of the first modality to the space of the medical image data of the second modality is calculated (Step S32).

A VOI is then defined from within the first modality (Step S33). The VOI may then be automatically copied from the space of the medical image data of the first modality to the space of the medical image data of the second modality using the calculated transformation matrix (Step S34). Radiotherapy may then be directed to the patient using the medical image data of the second modality with the copied VOI (Step S35). Alternatively, or additionally, the medical image data of the second modality with the copied VOI may be stored to a database for later recall.

According to embodiments of the present invention, the first-acquired medical image data may be image data of a previous study and the second-acquired medical image data may be image data of a current study. The VOI may be copied from the previous study to the current study for the purposes of comparing quantifications of the lesion from the previous study with the current study to track the procession of the lesion and/or to determine how the lesion may have changed. This comparison may help to determine the effectiveness of treatment and/or therapy that has been administered between the acquisition of the previous study and the acquisition of the current study.

The previous study may be pre-therapy and the current study may be post-therapy. Thus therapy may be applied between the time of the previous study and the current study. This certainly does not preclude the possibility that an additional application of therapy after the current study, after which another study (a future study) may be performed. In such a case the first two studies (the previous study and the current study) may be considered pre-therapy studies from the point of view of the additional therapy and the future study may be considered the post-therapy study. As a study may be post-therapy with respect to one therapy and pre-therapy with respect to another study, it should be understood that exemplary embodiments of the present invention may be applied accordingly.

According to an exemplary embodiment of the present invention, a patient may undergo a PET scan and VOIs may be defined for that PET scan based on the identification of a lesion. One week later, the patient may undergo a CT scan. Exemplary embodiments of the present invention may be used to create a counterpart VOI on the CT scan. A radiotherapy structure set object may then be created based on the CT scan with counterpart VOI to direct radiotherapy to the site of the lesion.

Figure 4:
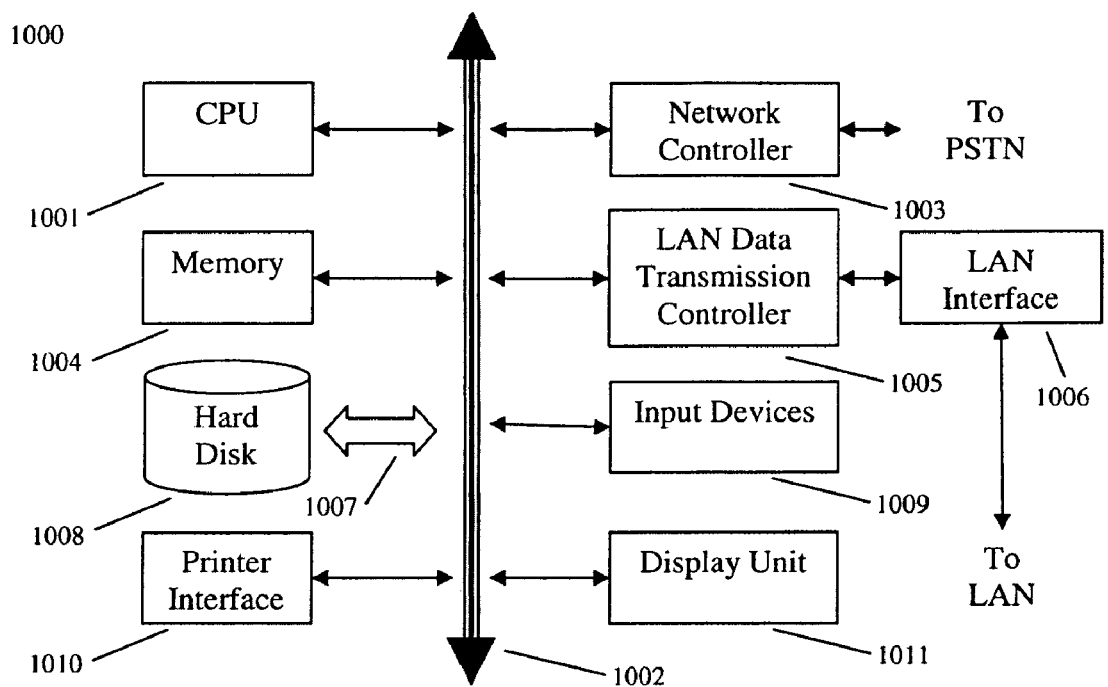
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for lesion detection, comprising:
acquiring medical image data from a first modality;
acquiring medical image data from a second modality;
calculating a transformation matrix for transforming from an image space of the first modality to an image space of the second modality;
defining a volume of interest from the medical image data of the first modality, wherein the volume of interest includes one or more lesions wherein defining a volume of interest includes:
defining the volume of interest based on one or more threshold values;
receiving user input including an adjustment to the one or more threshold values; and
redefining the volume of interest based on the adjusted one or more threshold values; and
automatically copying the volume of interest to the medical image data of the second modality using the calculated transformation matrix.

2. The method of claim 1, additionally including directing treatment based on structural information provided by the medical image data of the second modality and the volume of interest copied thereto.

3. The method of claim 2, wherein the treatment includes radiotherapy.

4. The method of claim 1, wherein the first modality is a functional modality and the second modality is a structural modality.

5. The method of claim 1, wherein the first modality is a PET or a SPECT and the second modality is a CT or MR.

6. The method of claim 1, wherein the volume of interest is defined from manual segmentation performed on one or more image slices of the medical image of the first modality.

7. The method of claim 1, wherein the volume of interest is defined from a placement of a predetermined shape within the medical image of the first modality.

8. The method of claim 1, additionally including creating a radiotherapy object for directing radiotherapy by marking the volume of interest on the image data first modality, wherein the first modality is a PET.

9. The method of claim 1, wherein redefining the volume of interest based on the adjusted threshold values is performed in real time by referring to a predetermined hash table.

10. A method for lesion tracking, comprising:
acquiring medical image data from a first modality at a first point in time;
defining a volume of interest from the medical image data of the first modality, wherein the volume of interest includes a lesion wherein defining a volume of interest includes:
defining the volume of interest based on one or more threshold values:
receiving user input including an adjustment to the one or more threshold values; and
redefining the volume of interest based on the adjusted one or more threshold values;
calculating one or more original quantified characteristics for the lesion based on the defined volume of interest;
acquiring medical image data from a second modality at a second point in time;
transforming the volume of interest to a second modality space and copying the transformed volume of interest to the medical image data of the second modality;
calculating one or more updated quantified characteristics for the lesion for the copied volume of interest within the medical image data of the second modality; and
comparing the one or more original quantified characteristics for the lesion with the one or more updated quantified characteristics for the lesion to determine how the lesion has changed from the first point in time to the second point in time.

11. The method of claim 10, wherein the first modality is a functional modality and the second modality is a structural modality.

12. The method of claim 10, wherein the first modality is a PET or a SPECT and the second modality is a CT or MR.

13. The method of claim 10, wherein the first point in time occurs prior to performance of a treatment and the second point in time occurs after the performance of the treatment and wherein the determination of how the lesion has changed from the first point in time to the second point in time is a determination of how the lesion has responded to the performance of the treatment.

14. The method of claim 10, wherein the volume of interest is defined from manual segmentation performed on one or more image slices of the medical image of the first modality.

15. The method of claim 10, wherein the volume of interest is defined from a placement of a predetermined shape within the medical image of the first modality.

16. The method of claim 10, wherein the one or more original quantified characteristics and the one or more updated quantified characteristics include a minimum feature size, a maximum feature size, or an average feature size.

* * * * *